(12) United States Patent
Nakajo et al.

(10) Patent No.: US 9,597,266 B2
(45) Date of Patent: Mar. 21, 2017

(54) GEL COMPOSITION FOR EXTERNAL APPLICATION CONTAINING AN ADENINE COMPOUND

(75) Inventors: Misato Nakajo, Otsu (JP); Fumiki Harano, Otsu (JP); Kosaburo Wakamatsu, Otsu (JP); Kazuhiro Yagyu, Kanonji (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 260 days.

(21) Appl. No.: 12/672,254

(22) PCT Filed: Aug. 4, 2008

(86) PCT No.: PCT/JP2008/063982
§ 371 (c)(1),
(2), (4) Date: Feb. 4, 2010

(87) PCT Pub. No.: WO2009/020104
PCT Pub. Date: Feb. 12, 2009

(65) Prior Publication Data
US 2011/0224163 A1  Sep. 15, 2011

(30) Foreign Application Priority Data
Aug. 6, 2007  (JP) ................................. 2007-204556

(51) Int. Cl.
| | | |
|---|---|---|
| *A61K 8/02* | (2006.01) | |
| *A61K 31/7076* | (2006.01) | |
| *A61K 9/00* | (2006.01) | |
| *A61K 47/36* | (2006.01) | |
| *A61K 8/60* | (2006.01) | |
| *A61K 9/70* | (2006.01) | |
| *A61K 31/52* | (2006.01) | |
| *A61K 47/10* | (2006.01) | |
| *A61K 47/18* | (2006.01) | |
| *A61Q 19/00* | (2006.01) | |
| *A61Q 19/08* | (2006.01) | |

(52) U.S. Cl.
CPC .......... *A61K 8/0208* (2013.01); *A61K 8/0212* (2013.01); *A61K 8/60* (2013.01); *A61K 8/606* (2013.01); *A61K 9/0014* (2013.01); *A61K 9/7007* (2013.01); *A61K 31/52* (2013.01); *A61K 31/7076* (2013.01); *A61K 47/10* (2013.01); *A61K 47/183* (2013.01); *A61K 47/36* (2013.01); *A61Q 19/00* (2013.01); *A61Q 19/08* (2013.01); *A61K 2800/88* (2013.01)

(58) Field of Classification Search
CPC ......................... A61K 8/0208; A61K 31/7076
See application file for complete search history.

(56) References Cited

U.S. PATENT DOCUMENTS

| 3,871,967 | A * | 3/1975 | Abdou et al. .............. 435/253.6 |
|---|---|---|---|
| 4,702,913 | A * | 10/1987 | Marty ........................... 424/579 |
| 7,037,514 | B1 * | 5/2006 | Horizumi et al. ............ 424/402 |
| 7,531,185 | B2 | 5/2009 | Chen et al. |
| 8,492,353 | B2 | 7/2013 | Wakamatsu et al. |
| 2003/0044439 | A1 * | 3/2003 | Dobson et al. .............. 424/401 |
| 2004/0018166 | A1 * | 1/2004 | Chen et al. ................ 424/70.16 |
| 2004/0161435 | A1 | 8/2004 | Gupta |
| 2004/0219124 | A1 | 11/2004 | Gupta |
| 2005/0250710 | A1 * | 11/2005 | Wakamatsu et al. .......... 514/27 |
| 2007/0135374 | A1 | 6/2007 | Shinohara et al. |

FOREIGN PATENT DOCUMENTS

| EP | 1512405 A1 | 3/2005 |
|---|---|---|
| JP | 2000-226325 A | 8/2000 |
| JP | 2002-234830 | 8/2002 |
| JP | 2003-40793 | 2/2003 |
| JP | 2003-063924 | 3/2003 |
| JP | 2003-334212 | 11/2003 |
| JP | 2005-272645 | 10/2005 |
| JP | 2005-320264 | 11/2005 |
| JP | 2005-535677 | 11/2005 |
| JP | 2006-056543 | 3/2006 |
| JP | 2006-182746 | 7/2006 |
| JP | 2007-176798 A | 5/2007 |
| KR | 10-2006-0132817 A | 12/2006 |
| TW | 200406228 A | 8/1992 |
| TW | 200427470 A | 10/1992 |
| WO | WO 01/02478 A1 | 1/2001 |
| WO | WO 2004/039358 A1 | 5/2004 |

OTHER PUBLICATIONS

Machine translation of Foreign Patent JP 2003-063924 A, http://dossier1.ipdl.inpit.go.jp/, accessed online on Aug. 2, 2012.*

(Continued)

*Primary Examiner* — Jonathan S Lau
(74) *Attorney, Agent, or Firm* — Finnegan, Henderson, Farabow, Garrett & Dunner, L.L.P.

(57) ABSTRACT

An object of the present invention is to provide a composition for external application that is applied to a part of the skin to more effectively elicit the useful effects of an adenine compound such as adenine, adenosine, and a phosphoric ester of adenosine, and that has long-lasting effects and enhanced skin-moisturizing effects. A gel composition for external application containing an adenine compound such as adenine, adenosine, and a phosphoric ester of adenosine is prepared by using agar as a gelling agent. The gel composition is further prepared in the form of a sheet-like adhesive patch. The gel composition in the form of a sheet-like adhesive patch is kept immersed in an aqueous solution containing the adenine compound.

8 Claims, 2 Drawing Sheets

(56) References Cited

OTHER PUBLICATIONS

Saiki, T., J. Biol. Chem., 1906, 2, p. 251-265.*
Machine translation of Foreign Patent JP 2006-056543 A, http://dossier1.ipdl.inpit.go.jp/, accessed online on Aug. 2, 2012.*
Definition of diffusion, Merriam-Webster dictionary, http://www.merriam-webster.com, accessed online on Jun. 3, 2014.*
Definition of "immerse", Oxford English Dictionary, http://www.oed.com, accessed online on Oct. 31, 2016.*
Definition of "dip", Oxford English Dictionary, http://www.oed.com, accessed online on Oct. 31, 2016.*
English language machine translation of JP 2007-176798 A.
English language Abstract of KR10-2006-0132817A.
Supplementary European Search Report in counterpart European Application No. 08792179.7 mailed Jun. 24, 2015.
Office Action for corresponding JP Application No. 2015-118600 dated Dec. 20, 2016.

* cited by examiner

GEL COMPOSITION FOR EXTERNAL APPLICATION CONTAINING AN ADENINE COMPOUND

TECHNICAL FIELD

The present invention relates to a gel composition (a gel-like composition) for external application containing an adenine compound selected from the group consisting of adenine, adenosine, and phosphoric esters of adenosine. More particularly, the present invention relates to a gel composition for external application that effectively elicits useful effects from an adenine compound, and that exhibits long-lasting effects and enhanced skin-moisturizing effects.

BACKGROUND ART

Adenine compounds such as adenine, adenosine, and phosphoric esters of adenosine are known to have various useful effects, such as skin pigmentation reduction and skin-aging prevention, and are used as an active ingredient in compositions for external application. Examples of known compositions containing an adenine compound include an O/W emulsion composition (see Patent Document 1) and a solid composition comprising an oil-in-water emulsion (see Patent Document 2).

The composition for external application to the skin in the form of an adhesive patch is required to have a good adhesion to the skin and provide a comfortable feel when used, in addition to eliciting a desired effect from the active ingredient. However, there has been no report of an adenine compound-containing composition for external application to the skin in the form of an adhesive patch that is satisfactory in terms of all of: elicitation of useful effects from an adenine compound; adhesion to the skin; and comfortable feel when used.

Furthermore, there is no known product for external application containing a gel composition for external application immersed in an aqueous solution containing an active ingredient. What properties are imparted to the gel composition for external application provided in such an immersed state are also unknown.

With the recent trend toward more diverse and advanced physiological effects required of compositions for external application under the above-mentioned background of the prior art, there has been a demand for the development of a composition for external application in a form capable of eliciting useful effects from an adenine compound more effectively and sustainably.

Patent Document 1: Japanese Unexamined Patent Publication No. 2002-234830
Patent Document 2: Japanese Unexamined Patent Publication No. 2006-182746

DISCLOSURE OF THE INVENTION

Problem to be Solved by the Invention

An object of the present invention is to provide a composition for external application that has excellent adhesion to the skin when applied to the skin as an adhesive patch, that can more effectively elicit useful effects from an adenine compound such as adenine, adenosine, or a phosphoric ester of adenosine, and that exhibits long-lasting effects and enhanced skin-moisturizing effects. Another object of the present invention is to provide a product for external application that can be used as a cosmetic, pharmaceutical, or the like capable of more effectively eliciting the above-mentioned effects of the composition for external application.

Means for Solving the Problem

The present inventors conducted extensive research to solve the above problems. As a result, the inventors found that when a gel composition for external application containing an adenine compound, such as adenine, adenosine, or a phosphoric ester of adenosine, is produced by using agar as a gelling agent, the functions of the adenine compound can be elicited effectively and sustainably. Particularly, when a phosphoric ester of adenosine is used as the adenine compound, the skin pigmentation inhibitory effects and skin aging prevention (water retention, flexibility, increase in skin brightness (dullness prevention), turnover promotion) effects, which are functions of a phosphoric ester of adenosine, can be elicited more effectively and sustainably. The inventors further found that when the gel composition for external application is prepared in the form of a sheet-like adhesive patch, the resulting product has improved visibility, and enhanced skin moisturizing effects and adhesion to the skin. The inventors further found that when the gel composition for external application in the form of a sheet-like adhesive patch is kept immersed in an aqueous solution containing an adenine compound, the functions of the adenine compound can be more effectively elicited, and the skin moisturizing effects and adhesion to the skin can be more effectively enhanced. The present invention has been achieved by further improvements based on this finding.

More specifically, the present invention provides the following modes of the invention.

Item 1. A gel composition (a gel-like composition) for external application comprising agar and at least one adenine compound selected from the group consisting of adenine, adenosine, and phosphoric esters of adenosine.

Item 2. The gel composition for external application according to item 1, wherein the adenine compound is at least one phosphoric ester of adenosine selected from the group consisting of adenosine 3',5'-cyclic phosphoric acid, adenosine monophosphate, adenosine diphosphate, adenosine triphosphate, and salts thereof.

Item 3. The gel composition for external application according to item 1, wherein the adenine compound is at least one member selected from the group consisting of adenosine monophosphate, and salts thereof.

Item 4. The gel composition for external application according to item 1, further comprising a polyhydric alcohol.

Item 5. The gel composition for external application according to item 1, containing the adenine compound in an amount of 0.1 wt. % or more.

Item 6. The gel composition for external application according to item 1, containing the agar in an amount of 0.5 to 5 wt. %.

Item 7. The gel composition for external application according to item 1, which is in the form of a sheet-like adhesive patch.

Item 8. The gel composition for external application according to item 7, which has a thickness of 0.5 to 1 mm.

Item 9. A preparation for external application comprising the gel composition for external application of item 1, and an aqueous solution containing at least one adenine compound selected from the group consisting of adenine, adenosine, and phosphoric esters of adenosine, the gel composition being kept immersed in the aqueous solution.

Item 10. A product for external application comprising a container in which the gel composition for external application of item 1 is kept immersed in an aqueous solution containing at least one adenine compound selected from the group consisting of adenine, adenosine, and phosphoric esters of adenosine.

Item 11. The product for external application according to item 10, wherein the container has a recess in which the gel composition for external application according to item 1 is kept immersed in an aqueous solution containing at least one adenine compound selected from the group consisting of adenine, adenosine, and phosphoric esters of adenosine, the recess of the container being hermetically sealed with a cover in an openable manner.

Item 12. The product for external application according to item 10, wherein the gel composition is in the form of a sheet-like adhesive patch.

Item 13. Use of a gel composition comprising agar and at least one adenine compound selected from the group consisting of adenine, adenosine, and phosphoric esters of adenosine to produce an anti-aging composition for external application.

Effect Of The Invention

The gel composition (the gel-like composition) for external application of the present invention enhances the permeability of an adenine compound into the skin, and thus can effectively elicit the functions of the adenine compound. The gel composition for external application of the present invention is particularly useful for eliciting the functions of phosphoric esters of adenosine, so that water retention, an increase in softness, pigmentation reduction (reduction in the amount of melanin), an increase in skin brightness (dullness prevention), turnover promotion, etc. which are anti-aging effects of phosphoric esters of adenosine, can be elicited effectively and sustainably.

The gel composition for external application of the present invention formed into a sheet-like adhesive patch has improved visibility (visual recognizability), and enhanced skin moisturizing effects and adhesion to the skin, and is therefore particularly useful.

Furthermore, the product for external application containing the gel composition for external application of the present invention in a state immersed in an aqueous solution containing an adenine compound can particularly effectively elicit the functions of the adenine compound, and also more effectively provides enhanced skin moisturizing effects and improved adhesion to the skin. Accordingly, the product is particularly suitable for use in maintaining skin health and beauty. The gel composition withdrawn from the aqueous solution containing an adenine compound characteristically has an appropriately wet surface; based on this feature, the composition has excellent adhesion to the skin. Therefore, even when directly applied to the skin, the composition is stably retained at the site of application to the skin without falling off the skin.

BEST MODE FOR CARRYING OUT THE INVENTION

Figure 1:
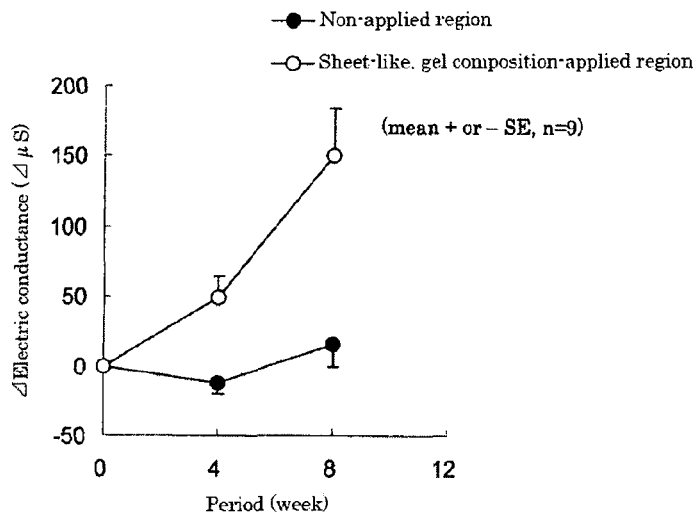
FIG. 1 shows the evaluation results of the moisture content (electric conductance) obtained in Test Example 1.

I. Gel Composition (Gel-Like Composition) for External Application

The gel composition for external application according to the present invention comprises agar and at least one adenine compound selected from the group consisting of adenine, adenosine, and phosphoric esters of adenosine. The gel composition for external application of the present invention is described in detail below.

The gel composition for external application of the present invention contains at least one adenine compound selected from the group consisting of adenine, adenosine and phosphoric esters of adenosine.

Among the above-mentioned adenine compounds, phosphoric esters of adenosine are not particularly limited as long as they can be incorporated into cosmetics, drugs or quasi-drugs for external application. Specific examples of phosphoric esters of adenosine include adenosine 3',5'-cyclic phosphoric acid, adenosine monophosphate [adenosine 2'-phosphoric acid, adenosine 3'-phosphoric acid, adenosine 5'-phosphoric acid (AMP)], adenosine diphosphate, adenosine triphosphate, and salts thereof. Such phosphoric esters of adenosine may be used singly, or in a combination of two or more.

Salts of phosphoric esters of adenosine are not particularly limited as long as they can be incorporated into cosmetics, drugs or quasi drugs for external application. Specific examples of salts of phosphoric esters of adenosine include alkali metal salts such as sodium salts and potassium salts; alkaline earth metal salts such as calcium salts, magnesium salts, and barium salts; basic amino acid salts such as arginine and lysine; ammonium salts such as ammonium salts and tricyclohexylammonium salts; various alkanolamine salts such as monoethanolamine salts, diethanolamine salts, triethanolamine salts, monoisopropanolamine salts, diisopropanolamine salts, and triisopropanolamine salts. Preferable salts are alkali metal salts such as sodium salts. Examples of preferable alkali metal salts include adenosine monophosphate monosodium and adenosine monophosphate disodium. Such salts of phosphoric esters of adenosine can be used singly, or in a combination of two or more.

The gel composition for external application of the present invention may contain one, or two or more types of adenosine compounds.

Among the above-mentioned adenosine compounds, phosphoric esters of adenosine, especially AMP and salts thereof, can impart particularly excellent anti-aging effects to the gel composition for external application of the present invention, and are therefore preferable.

The amount of adenosine compound in the gel composition for external application of the present invention can be appropriately selected according to the stability of the gel composition for external application, the influence on the gel strength, the expected effects, etc. The adenine compound can be used, for example, in an amount of at least 0.1 wt. %, preferably 0.5 to 20 wt. %, and more preferably 1 to 10 wt. %, based on the total amount of the gel composition for external application.

The gel composition for external application of the present invention further contains an agar as a gelling agent. When the gel composition for external application produced by using an agar as a gelling agent is used in the form of an adhesive patch having excellent usability, the functions of an adenine compound, particularly the functions of a phosphoric ester of adenosine, can be effectively elicited for a long period of time. The amount of agar in the gel composition for external application of the present invention may vary according to factors such as the gel strength required of the gel composition for external application, and cannot be uniformly specified. The amount of agar is typically 0.5 to 5 wt. %, preferably 1 to 4 wt. %, and more preferably 1.5 to 3.0 wt. %, based on the total amount of the gel composition for external application.

The gel composition for external application of the present invention may contain a polyhydric alcohol, in addition to the above-mentioned adenine compound and agar. The polyhydric alcohol can impart skin-moisturizing effects and dry skin improvement effects to the gel composition for external application, and also enhance the adhesion to the skin. Further, the polyhydric alcohol plays a role as a plasticizer for improving the gel flexibility. The greatest particular advantage of using a polyhydric alcohol is simplification of the production process of the gel composition of the present invention. More specifically, if agar is directed added to water during the production process, agar, which has a high swelling property due to water absorption, becomes "lumpy", i.e., enters a state in which water is only absorbed on the surface of clusters of agar powder, but not inside thereof, thus resulting in undissolved agar. When agar dispersed in a polyhydric alcohol is added to water, lumps of agar are not formed, thus reducing the undissolved agar. The polyhydric alcohol that can be used in the present invention is not particularly limited. Specific examples of polyhydric alcohols include glycerol, polyglycerols having a polymerization degree of 2 to 10 (e.g., diglycerin, triglycerin, tetraglycerin, etc.), ethylene glycol, diethylene glycol, polyethylene glycol, 1,3-butylene glycol, propylene glycol, dipropylene glycol, isoprene glycol, pentadiol, sorbitol, maltitol, fructose, and the like. Glycerol is preferable among these alcohols, because it has particularly excellent effects as a polyhydric alcohol, and particularly enhances the adhesion to the skin and skin moisturizing effects. Such polyhydric alcohols may be used singly, or in a combination of two or more.

When a polyhydric alcohol is incorporated into the gel composition for external application of the present invention, the amount of polyhydric alcohol is not particularly limited. The amount of polyhydric alcohol is typically 1 to 30 wt. %, and preferably 5 to 20 wt. %, based on the total amount of the gel composition for external application. It is particularly preferable that the amount of polyhydric alcohol is 10 to 15 wt. %. When a polyhydric alcohol is used in an amount within this range, the resulting gel composition has particularly excellent flexibility and appropriate strength, and provides a comfortable feel without stickiness when applied to the skin because the formation of undissolved agar during the production process is remarkably inhibited.

The gel composition for external application of the present invention may contain, in addition to the above-mentioned components, appropriate amounts of various known components used in compositions applied to the skin or mucous membranes, such as cosmetics, drugs or quasi-drugs for external application. Examples of such components include surfactants, colorants (dyes, pigments), flavors, preservatives, bactericides (antimicrobial agents), thickeners, antioxidants, metal chelators, refrigerants, deodorants, film-forming agents, moistening agents, humectants, UV absorbers, UV dispersants, vitamins, plant extracts, skin astringents, anti-inflammatory agents (antiphlogistics), whitening agents, cell activators, vasodilators, blood circulation enhancers, and skin function accelerators. It is also possible to incorporate known bases and carriers, such as those exemplified above, according to the form of the composition.

Among these components, examples of surfactants include anionic surfactants such as higher fatty acid soaps, alkyl sulfonate ester salts, polyoxyethylene alkyl ether sulfates, alkyl ether phosphate ester salts, N-acylamino acid salts, and acyl N-methyl taurine salts, etc.; cationic surfactants such as alkyl trimethyl ammonium chlorides and dialkyl dimethyl ammonium chlorides, etc.; amphoteric surfactants such as alkyldimethylaminoacetic acid betaines, alkylamidedimethylaminoacetic acid betaines, and 2-alkyl-N-carboxy-N-hydroxyimidazolinium betaines, etc.; non-ionic surfactants such as polyoxyethylene surfactants, polyhydric alcohol ester surfactants, and ethylene oxide/propylene oxide block copolymers; etc. It is also possible to use polymeric surfactants and natural surfactants without particular limitation.

Examples of preservatives include ethyl parahydroxybenzoate, salicylic acid, sorbic acid, and the like. Examples of thickening agents include xanthane gum, sodium carboxymethylcellulose, carboxyvinyl polymers, and the like. Examples of metal chelators include sodium salts of ethylenediaminetetraacetic acid, phosphoric acid, citric acid, and the like.

The gel composition for external application of the present invention adheres to the skin, and therefore can be used in the form of an adhesive patch. The form of the gel composition for external application of the present invention is not particularly limited as long as it is in a form externally applicable to the skin, such as cosmetics, pharmaceuticals, or quasi-drugs for external application to the skin. The composition in the form of a sheet-like adhesive patch is preferable from the viewpoint of more preferable visibility, skin-moisturizing effects, and adhesion to the skin. When the gel composition for external application of the present invention is prepared in the form of a sheet-like adhesive patch, the thickness of the patch is not particularly limited. For example, a thickness of 0.5 to 1.0 mm is preferable from the viewpoint of excellent visibility and enhanced adhesion to the skin. When the thickness of the sheet-like adhesive patch is in the above-mentioned range, the patch applied to the skin does not fall off the skin due to the weight of the gel composition, and thus can advantageously provide an adenine compound of the gel composition to the skin for a long period of time. When the thickness of the patch is in the above-mentioned range, the gel composition for external application can maintain sufficiently high adhesion to the skin, even when the composition is kept immersed in an aqueous solution containing an adenine compound.

The form of the gel composition for external application of the present invention can be appropriately selected according to the skin application site to the skin. For example, when the gel composition for external application of the present invention is applied to a cheek or infraorbital (eye) region of a face, a preferable shape of the gel composition is roughly crescentic.

When the gel composition for external application of the present invention is applied to the skin, the composition produces blockage effects on the skin, whereby the adenine compound contained in a gel composition for external application can sustainably permeate into the skin and particularly effectively provide its useful effects to the skin.

Thus, the gel composition for external application of the present invention enhances the permeability of an adenine compound into the skin, and prolongs the effects of the adenine compound, so that the effects of the adenine compound provided to the skin, i.e., the skin-whitening and anti-aging effects, such as pigmentation inhibition (reduction in the amount of melanin), water retention, enhanced flexibility, increase in skin brightness (dullness prevention), and turnover promotion, etc. can be effectively exhibited. Accordingly, the gel composition of the present invention is useful as a cosmetic or drug for external application (including a quasi-drug for external application), and is preferably used as a whitening or anti-aging composition for external application (preferably cosmetics). It is particularly preferable that the gel composition for external application of the present invention is applied to a cheek or infraorbital (eye) region of a face to exhibit the above-mentioned effects of the adenine compound in this region.

When used, the gel composition for external application of the present invention is directly applied to the skin. The amount of the gel composition to be used and the number of uses per day can be appropriately selected according to the age and sex of the user, the purpose of use, the severity of the condition of skin, etc. For example, the composition may be applied to the skin one to five or six times per day. The length of time of the application of the composition to the skin per application may be, for example, about 10 to 15 minutes.

The method for producing the gel composition for external application of the present invention is not particularly limited. The composition can be produced by a method known in the art. A representative example of the production method comprises the following steps (1) to (3):
(1) adding a specific amount of water-swollen agar and heating to dissolve the agar;
(2) subsequently reducing the solution temperature to a temperature range in which agar is not solidified and the adenine compound is not affected, and then adding an adenine compound and optionally other additives in specific amounts to obtain a mixture; and
(3) forming the mixture into a desired shape and then cooling to form a gel.

II. Product for External Application

The gel composition for external application is preferably provided in the form of a product for external application comprising a container in which the gel composition is kept immersed in an aqueous solution containing an adenine compound (hereinafter sometimes simply referred to as a "medicinal solution"). The gel composition for external application formed into a product for external application can more effectively elicit the effects of an adenine compound, and can have enhanced skin-moisturizing effects and improved adhesion to the skin.

The form of the gel composition for external application contained in the product for external application is not particularly limited. The composition is preferably in a sheet-like form.

Examples of the adenine compound of the medicinal solution contained in the product for external application of the present invention may be the same as those described in the "I. Gel composition (Gel-like composition) for external application" section above.

The proportion of the adenine compound in the medicinal solution contained in the product for external application of the present invention is not particularly limited, and is typically at least 0.1 wt. %, preferably 0.5 to 20 wt. %, and more preferably 1 to 10 wt. %, based on the total weight of the medicinal solution. It is particularly preferable that the kind and proportion of the adenine compound in the medicinal solution are the same as those of the adenine compound in the gel composition for external application contained in the product for external application of the present invention. Since the medicinal solution and the gel composition for external application contain the same type of adenine compound in the same proportion, there is no concentration gradient between the gel composition and the medicinal composition, thus more effectively enhancing the permeability of the adenine compound into the skin, and more effectively imparting the desired functions to the gel composition for external application.

The medicinal solution contained in the external product (the product for external application) of the present invention may contain a polyhydric alcohol such as glycerol in addition to an adenine compound, as in the gel composition for external application. The medicinal solution may further contain appropriate amounts of various known components used in compositions applied to the skin or mucous membranes, such as cosmetics, drugs or quasi-drugs for external application. In order to stably maintain the constitution of the gel composition for external application during storage, the proportions of the components of the medicinal solution contained in the external product of the present invention are preferably the same as those of the gel composition for external application.

Although the number of gel compositions for external application housed in one container of the product for external application of the present invention is not particularly limited, the number is preferably one or the same as the number of gel compositions used per application, in order to prevent contamination after opening and inhibit compositional changes.

The ratio of the medicinal solution and the gel composition for external application housed in the container of the product for external application of the present invention is not particularly limited. For example, the amount of the medicinal composition is typically 1 to 200 parts by weight, preferably 10 to 100 parts by weight, and more preferably 10 to 40 parts by weight, per 100 parts by weight of the gel composition for external application.

More specifically, the product for external application of the present invention may comprise: a container having a recess; a gel composition for external application formed into a desired sheet-like shape; and a medicinal composition; the gel composition and the medicinal composition being housed in the recess of the container, and the recess being hermetically sealed with a cover in an openable manner. Although the capacity of the recess of the container is not particularly limited, it is preferably about 2.5 to about 4.5 times the volume of the gel composition for external application.

The gel composition for external application housed in the product for external application of the present invention is withdrawn from the container when used. Thus, according to the product for external application of the present invention, the gel composition for external application is kept immersed in a medicinal solution until immediately before use. Therefore, because compositional changes of the gel composition hardly occur during storage, the gel composition can advantageously be stably maintained.

When the moisture content of the skin contact surface of the gel composition for external application is excessively high or excessively low, the composition does not have sufficient adhesion to the skin. As a result, even when the gel composition for external application is brought into contact with the skin, the composition falls off the site of application to the skin, and cannot be stably retained. To provide a gel composition for external application with good adhesion to the skin, it is important that the skin contact surface of the gel composition for external application is appropriately humidified. The product for external application of the present invention contains the gel composition for external application in a state immersed in a medicinal solution, and, when used, the gel composition is withdrawn from the medicinal solution. Accordingly, the gel composition for external application immediately after withdrawal from the medicinal solution has an appropriately humidified surface, and therefore has advantageously excellent adhesion to the skin.

As described above, various advantages can be provided by keeping the gel composition for external application immersed in the medicinal composition. Thus, as another aspect of the present invention, the present invention further provides a preparation for external application comprising the gel composition for external application kept immersed in the medicinal solution. The preparation for external application contains the gel composition for external application and the medicinal solution in such a state that the gel composition is immersed in the medicinal solution. A specific constitution thereof may be the same as that of the components (i.e., the above-mentioned gel composition for external application and medicinal solution) housed in the container of the above-mentioned product for external application.

EXAMPLES

The present invention will be described below in more detail with reference to Examples and Test Examples. However, the present invention is not limited thereto or thereby.

Example 1

1. Preparation of a Sheet-Like, Gel Composition for External Application

A sheet-like, gel composition for external application (thickness: 0.9 mm, surface area: 11.4 cm², weight per sheet: 1.0 g) was prepared according to the following formulation.

|  | (wt. %) |
| --- | --- |
| AMP 2Na | 3.0 |
| Powdered agar | 3.0 |
| Glycerol | 24.5 |
| Film-forming agent | 0.9 |
| Preservative | q.s. |
| pH adjuster | q.s. |
| Purified water | balance |
|  | 100 |

2. Preparation of a Medicinal Solution

A medicinal solution was prepared according to the following formulation.

|  | (wt. %) |
| --- | --- |
| AMP 2Na | 3.0 |
| Glycerol | 10.0 |

-continued

|  | (wt. %) |
| --- | --- |
| Preservative | q.s. |
| pH adjuster | q.s. |
| Purified water | balance |
|  | 100 |

3. Preparation of a Product for External Application 0.2 ml of the above medicinal solution was housed in the recess (depth: 2.6 mm, base area: 14.5 cm²) of a recessed plastic container, where one sheet-like, gel composition for external application as mentioned above was also housed. The recess was then hermetically sealed with a cover by heat-sealing. As a result, a product for external application was obtained.

Example 2

1. Preparation of a Sheet-Like, Gel Composition for External Application

A sheet-like, gel composition for external application (thickness: 0.9 mm, surface area: 11.4 cm², weight per sheet: 1.0 g) was prepared according to the following formulation.

|  | (wt. %) |
| --- | --- |
| AMP 2Na | 3.0 |
| Powdered agar | 3.0 |
| Glycerol | 15.0 |
| Moistening agent | q.s. |
| Film-forming agent | q.s. |
| Preservative | q.s. |
| pH adjuster | q.s. |
| Purified water | balance |
|  | 100 |

2. Preparation of a Medicinal Solution

A medicinal solution was prepared according to the following formulation.

|  | (wt. %) |
| --- | --- |
| AMP 2Na | 3.0 |
| Glycerol | 3.0 |
| Moistening agent | q.s. |
| Preservative | q.s. |
| pH adjuster | q.s. |
| Purified water | balance |
|  | 100 |

3. Preparation of a Product for External Application

The above medicinal solution and sheet-like, gel composition for external application were housed in the recess of a plastic container, and the recess was hermetically sealed with a cover by heat-sealing in the same manner as in Example 1. As a result, a product for external application was obtained.

Example 3

1. Preparation of a Sheet-Like, Gel Composition for External Application

A sheet-like, gel composition for external application (thickness: 0.9 mm, surface area: 11.4 cm², weight per sheet: 1.0 g) was prepared according to the following formulation.

| | (wt. %) |
|---|---|
| AMP 2Na | 10.0 |
| Powdered agar | 3.0 |
| Glycerol | 15.0 |
| Moistening agent | q.s. |
| Film-forming agent | q.s. |
| Preservative | q.s. |
| pH adjuster | q.s. |
| Purified water | balance |
| | 100 |

2. Preparation of a Medicinal Solution

A medicinal solution was prepared according to the following formulation.

| | (wt. %) |
|---|---|
| AMP 2Na | 10.0 |
| Glycerol | 3.0 |
| Moistening agent | q.s. |
| Preservative | q.s. |
| pH adjuster | q.s. |
| Purified water | balance |
| | 100 |

3. Preparation of a Product for External Application

The above medicinal solution and sheet-like, gel composition for external application were housed in the recess of a plastic container, and the recess was hermetically sealed with a cover by heat-sealing in the same manner as in Example 1. As a result, a product for external application was obtained.

Example 4

1. Preparation of a Sheet-Like, Gel Composition for External Application

A sheet-like, gel composition for external application (thickness: 0.9 mm, surface area: 11.4 cm$^2$, weight per sheet: 1.0 g) was prepared according to the following formulation.

| | (wt. %) |
|---|---|
| AMP 2Na | 3.0 |
| Powdered agar | 3.0 |
| Propylene glycol | 13.0 |
| Moistening agent | q.s. |
| Film-forming agent | q.s. |
| Preservative | q.s. |
| pH adjuster | q.s. |
| Purified water | balance |
| | 100 |

2. Preparation of a Medicinal Solution

A medicinal solution was prepared according to the following formulation.

| | (wt. %) |
|---|---|
| AMP 2Na | 10.0 |
| Propylene glycol | 3.0 |
| Moistening agent | q.s. |
| Preservative | q.s. |
| pH adjuster | q.s. |
| Purified water | balance |
| | 100 |

3. Preparation of a Product for External Application

The above medicinal solution and the above sheet-like, gel composition for external application were housed in the recess of a plastic container, and the recess was hermetically sealed with a cover by heat-sealing in the same manner as in Example 1. As a result, a product for external application was obtained.

Example 5

1. Preparation of a Sheet-Like, Gel Composition for External Application

A sheet-like, gel composition for external application (thickness: 0.9 mm, surface area: 11.4 cm$^2$, weight per sheet: 1.0 g) was prepared according to the following formulation.

| | (wt. %) |
|---|---|
| AMP 2Na | 3.0 |
| Powdered agar | 3.0 |
| 1,3-Butylene glycol | 10.0 |
| Moistening agent | q.s. |
| Film-forming agent | q.s. |
| Preservative | q.s. |
| pH adjuster | q.s. |
| Purified water | balance |
| | 100 |

2. Preparation of a Medicinal Solution

A medicinal solution was prepared according to the following formulation.

| | (wt. %) |
|---|---|
| AMP 2Na | 3.0 |
| 1,3-Butylene glycol | 2.5 |
| Moistening agent | q.s. |
| Preservative | q.s. |
| pH adjuster | q.s. |
| Purified water | balance |
| | 100 |

3. Preparation of a Product for External Application

The above medicinal solution and sheet-like, gel composition for external application were housed in the recess of a plastic container, and the recess was hermetically sealed with a cover by heat-sealing in the same manner as in Example 1. As a result, a product for external application was obtained.

Test Example 1

Evaluation of the Product for External Application Obtained in Example 1

The sheet-like, gel composition for external application was withdrawn from the product for external application obtained in Example 1, and applied, from the infraorbital region to the cheek region, to one side of a human face for 15 minutes. The composition was not applied to the other side of the face. The sheet-like, gel composition was applied once every 2 days for 8 consecutive weeks. The moisture content (electric conductance), melanin index, and skin brightness of the sheet-like, gel composition-applied side of the face and those of the non-applied side of the face were measured before the start of application, 4 weeks after the start of application, and 8 weeks after the start of application. The stratum corneum cell area was measured before application and 8 weeks after the start of application. The flexibility was measured 8 weeks after the start of the application. After the measurement site (face) was washed and each subject was then rested in a room at a temperature of 20° C. and a relative humidity of 50% for 30 minutes, the measurement was performed. Each test was conducted using 9 subjects (n=9). Each item was evaluated according to the following method.

<Evaluation of the Moisture Content (Electric Conductance)>

The electric conductance of the sheet-like, gel composition-applied region and the non-applied region was measured using a SKICON-200 (IBS) before the start of application, 4 weeks after the start of application, and 8 weeks after the start of application. The difference (Δ electric conductance, $\Delta \mu S$) between the electric conductance before the start of application and the electric conductance measured after the start of application was calculated to evaluate the effect on the skin moisture content.

<Evaluation of Flexibility (Frequency Change, Hz)>

The flexibility of the sheet-like, gel composition-applied skin region and the non-applied region was measured using a "Venustron" tactile sensor (AXIOM) 8 weeks after the start of application. The measurement was performed at a probe speed of 2 mm/sec and a depth of 5 mm. At the time of analysis, the Tactile Δf (Hz) at a pressure of 6 g was read to determine the flexibility. The tactile sensor Venustron is a device that determines flexibility by bringing a test substance into contact with a probe that vibrates at a constant frequency and measuring the change in frequency (Δf (Hz)). When the test substance is harder, the Δf becomes greater (shift in the positive direction), while when the test substance is softer, the Δf becomes smaller (shift in the negative direction).

<Evaluation of Melanin Index>

The melanin index of the sheet-like, gel composition-applied region and the non-applied region was measured using a "Mexameter" (Courage+Khazaka Electronics GmbH) before the start of application, 4 weeks after the start of application, and 8 weeks after the start of application. The "Mexameter" is a device that irradiates skin with three different wavelengths (568, 660, and 880 nm) of light, and measures the reflectance of light of 660 and 880 nm reflected from the skin to calculate the melanin index. The difference (Δ melanin index) between the melanin index before the start of application and the melanin index measured after the start of application was calculated to evaluate the effect on the amount of melanin.

<Evaluation of Skin Brightness>

The skin brightness (L* value) of the sheet-like, gel composition-applied region and the non-applied region was measured using an OFC-300A color difference meter (a product of Nippon Denshoku Industries Co., Ltd.) before the start of application, 4 weeks after the start of application, and 8 weeks after the start of application. The difference (Δ brightness, ΔL*) between the L* value before the start of application and the L* value measured after the start of application was calculated to evaluate the effect on the skin brightness.

<Evaluation of the Stratum Corneum Cell Area>

The stratum corneum cells of the sheet-like, gel composition-applied region and the non-applied region were sampled by a tape-stripping method before the start of application and 8 weeks after the start of application. After staining, the stratum corneum cell area was measured using an optical microscope and an image analyzer. The difference (Δ stratum corneum cell area, $\Delta \mu m^2$) between the stratum corneum cell area before the start of the application and the stratum corneum cell area measured after the start of application was calculated to evaluate the effect on the stratum corneum cell area.

Figure 2:
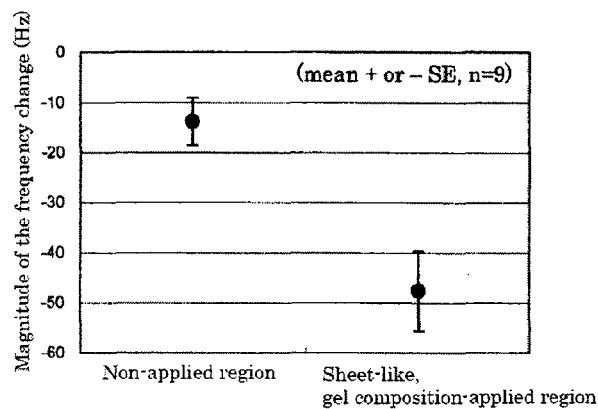
FIG. 2 shows the evaluation results of the flexibility (frequency change, Hz) obtained in Test Example 1.
Figure 3:
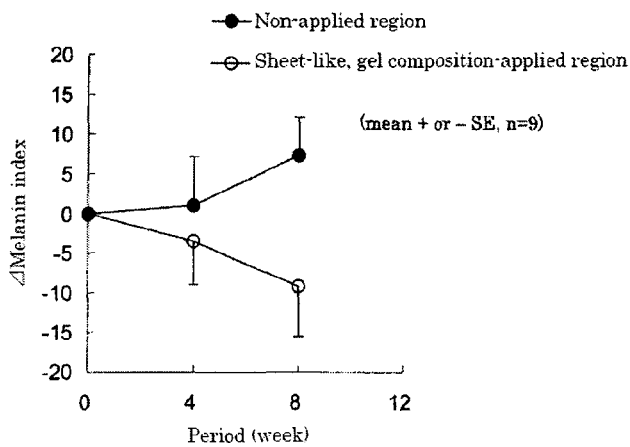
FIG. 3 shows the evaluation results of the melanin index obtained in Test Example 1.
Figure 4:
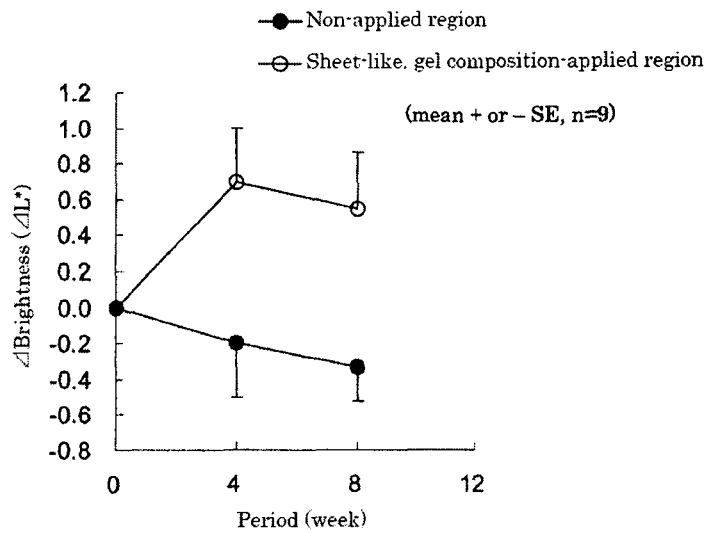
FIG. 4 shows the evaluation results of the skin brightness obtained in Test Example 1.
Figure 5:
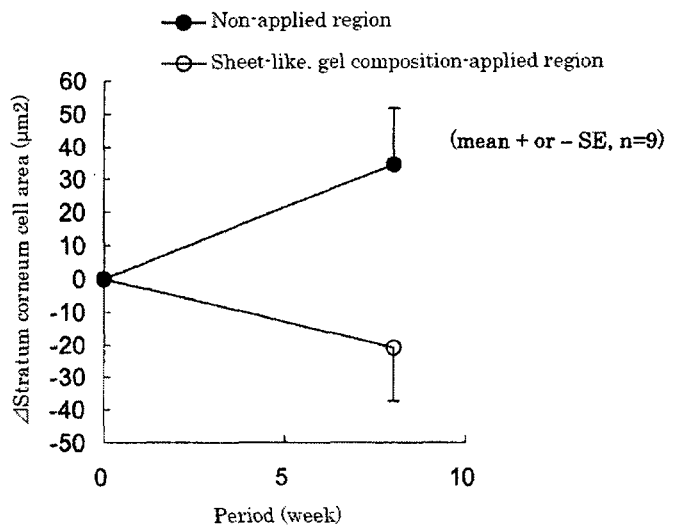
FIG. 5 shows the evaluation results of the stratum corneum cell area obtained in Test Example 1.

FIGS. 1 to 5 show the test results. FIGS. 1 to 5 clearly show that, compared to the non-applied region, a significant increase in the moisture content, increase in the flexibility, reduction in the melanin index, increase in the skin brightness, and reduction in the stratum corneum cell area were observed in the sheet-like, gel composition-applied region. Thus, the results confirmed that the physiological effects of AMP are more effectively exhibited. The results obtained using the sheet-like, gel composition for external application are remarkably higher than the effects expected from the single use of AMP. In this test, excellent adhesion of the sheet-like, gel composition to the skin was also confirmed; the composition did not fall off or move from the site of application to the skin during the application, and remained stably attached to the skin. The above results clearly show that when a phosphoric ester of adenosine is incorporated into a gel composition for external application produced using agar as a gelling agent, physiological functions of the phosphoric ester of adenosine can be more effectively exhibited.

Test Example 2

Evaluation of the Product for External Application Obtained in Example 2

The moisture content, melanin index, and skin brightness of the product for external application obtained in Example 2 were measured in the same manner as in Test Example 1.

The evaluation results of the moisture content, melanin index, and skin brightness of the product for external application obtained in Example 2 were equivalent to those of the product obtained in Example 1. It was also confirmed that the sheet-like, gel composition for external application withdrawn from the product for external application obtained in Example 2 has good adhesion to the site of application to the skin, and remains stably attached to the skin.

The invention claimed is:

1. A product for external application comprising a gel composition comprising agar and a first adenine compound selected from the group consisting of adenosine monophosphate and salts thereof in a form of a sheet-like adhesive patch suitable for applying to the skin, wherein the first adenine compound is contained in an amount of 0.5 to 20 wt. %. and the gel composition is kept immersed in an aqueous solution containing a second adenine compound selected from the group consisting of adenosine monophosphate and salts thereof, wherein the second adenine compound is present in the aqueous solution in a same proportion as the first adenine compound is present in the gel composition.

2. The product for external application according to claim 1, further comprising a polyhydric alcohol.

3. The product for external application according to claim 1, wherein the gel composition and the aqueous solution contain the adenine compound in an amount of 1 to 10 wt. % respectively.

4. The product for external application according to claim 1, containing the agar in an amount of 0.5 to 5 wt. %.

5. The product for external application according to claim 1, wherein the patch has a thickness of 0.5 to 1 mm.

6. A product comprising a container which houses the product for external application of claim 1.

7. The product according to claim 6, wherein the container has a recess which houses the product for external application according to claim 1, the recess of the container being hermetically sealed with a cover in an openable manner.

8. A method for treating aging of the skin which comprises applying to the skin of a person in need thereof a gel composition for external application obtained from the product of claim 1.

\* \* \* \* \*